United States Patent [19]

Barnes et al.

[11] Patent Number: 4,695,462

[45] Date of Patent: Sep. 22, 1987

[54] CELLULAR ENCAPSULATION OF BIOLOGICAL PESTICIDES

[75] Inventors: Andrew C. Barnes, San Diego; Susan G. Cummings, Chula Vista, both of Calif.

[73] Assignee: Mycogen Corporation, San Diego, Calif.

[21] Appl. No.: 750,369

[22] Filed: Jun. 28, 1985

[51] Int. Cl.⁴ .............................................. A01N 65/00
[52] U.S. Cl. ............................ 424/195.1; 424/DIG. 8
[58] Field of Search ................. 424/195.1, 93, DIG. 8

[56] References Cited

U.S. PATENT DOCUMENTS 4,265,880  5/1981  Spence et al. ........................... 424/93

FOREIGN PATENT DOCUMENTS 51-5047  2/1976  Japan .

OTHER PUBLICATIONS

West, A. W., (1984), Fate of the Insecticidal, Protein-aceous Parasporal Crystal of *B. thuringiensis* in Soil, Soil Biol. Biochem., 16:357-360.

West, A. W. et al., (1984), Detection of *B. thuringiensis* in Soil by Immunofluorescence, J. of Invertebrate Pathology, 43:150-155.

*Primary Examiner*—J. R. Brown
*Assistant Examiner*—John W. Rollins
*Attorney, Agent, or Firm*—Roman Saliwanchik; David R. Saliwanchik

[57]  ABSTRACT

The subject invention concerns pesticides comprising naturally-occurring pesticide-producing microorganisms, and the use thereof. Specifically, naturally-occurring pesticide-producing microorganisms are treated, for example with reagents, such as halogenating reagents, that prolong the activity of the pesticide produced in the cell, when the cell is applied to the environment of target pest(s).

20 Claims, No Drawings

CELLULAR ENCAPSULATION OF BIOLOGICAL PESTICIDES

BACKGROUND OF THE INVENTION

The extraordinary increase in agricultural productivity has been a result of many factors, including significantly better understanding of the methods involved with agriculture, improved equipment, availability of fertilizers, and improved pesticides. The latter factor has not been without detrimental aspects, however, due to the negative effect on the environment. There is, therefore, a substantial interest in developing effective and environmentally acceptable pesticides.

Among ecologically acceptable pesticides are the protein toxins produced by various microorganisms, such as *Bacillus thuringiensis*. However, the use of *B. thuringiensis* lysate or spores as a pesticide has significant drawbacks. The lifetime of the pesticide is relatively short in the environment, requiring multiple applications to give adequate protection. Consequently, these pesticides are not economical in comparison to more traditional chemical products having long residual activities. Improvements in field longevity would greatly aid in expanding the application of biological, or protein toxin-based pesticides.

West, Soil Biol. Biochem. (1984) 16:357-360 reports the results of a study on the persistence of *B.t.* toxin in soil. See also, West et al., J. of Invertebrate Pathology (1984) 43:150-155. U.S. Pat. No. 4,265,880 describes embedding live insecticidal pathogens in a coacervate microbead. Japanese Patent No. 51-5047 describes physical-chemical methods for killing *B. thuringiensis* spores, while retaining toxicity.

BRIEF SUMMARY OF THE INVENTION

Methods and compositions are disclosed for protecting agricultural crops and products from pests. Whole, i.e., unlysed, cells of a toxin (pesticide)-producing organism are treated with reagents that prolong the activity of the toxin produced in the cell when the cell is applied to the environment of target pest(s). The resulting naturally encapsulated pesticide may then be formulated in accordance with conventional techniques for application to the environment hosting a target pest, e.g., soil, water, and foliage of plants.

DETAILED DESCRIPTION OF THE INVENTION

In accordance with the subject invention, improved pesticides are provided, having among their other advantages an extended residual life, by modifying naturally-occurring pesticide-producing microorganisms. The subject method involves treating the organisms with reagents that prolong the activity of the toxin produced in the cell when the cell is applied to the environment of target pest(s). The resulting product retains the toxicity of the toxin.

The pesticide can be any toxin produced by a microbe. For example, it can be a polypeptide which has toxic activity toward a eukaryotic multicellular pest, such as insects, e.g., coleoptera, lepidoptera, diptera, hemiptera, dermaptera, and orthoptera; or arachnids; gastropods; or worms, such as nematodes and platyhelminths. Various susceptible insects include beetles, moths, flies, grasshoppers, lice, and earwigs.

The pesticide made in the host cell can be a polypeptide produced in active form or a precursor or proform requiring further processing for toxin activity, e.g., the crystal toxin of *B. thuringiensis* var. *kurstaki*, which requires processing by the pest.

Among naturally-occurring toxins are the polypeptide crystal toxins of *B. thuringiensis* var. *kurstaki*, active against lepidoptera; *B.t.* var. *israelensis*, active against mosquitoes; *B.t.* M-7, active against coleoptera; and *B. sphaericus*, active against mosquito larvae. Other toxins include those of entomopathogenic fungi, such as beauverin of *Beauveria bassiana* and destruxins of *Metarrhizium* spp.; or the broad spectrum insecticidal compounds, such as the avermectins of *Streptomyces avermitilus*. Cultures exemplifying the above are as follows:

Bacillus thuringiensis var. kurstaki HD-1—NRRL B-3792; disclosed in U.S. Pat. No. 4,448,885
Bacillus thuringiensis var. israelensis—ATCC 35646
Bacillus thuringiensis M-7—NRRL B-15939

The following *B. thuringiensis* cultures are available from the United States Department of Agriculture (USDA) at Brownsville, Tex. Requests should be made to Joe Garcia, USDA, ARS, Cotton Insects Research Unit, P.O. Box 1033, Brownsville, Tex. 78520 USA.

B. thuringiensis HD2
B. thuringiensis var. finitimus HD3
B. thuringiensis var. alesti HD4
B. thuringiensis var. kurstaki HD73
B. thuringiensis var. sotto HD770
B. thuringiensis var. dendrolimus HD7
B. thuringiensis var. kenyae HD5
B. thuringiensis var. galleriae HD29
B. thuringiensis var. canadensis HD224
B. thuringiensis var. entomocidus HD9
B. thuringiensis var. subtoxicus HD109
B. thuringiensis var. aizawai HD11
B. thuringiensis var. morrisoni HD12
B. thuringiensis var. ostriniae HD501
B. thuringiensis var. tolworthi HD537
B. thuringiensis var. darmstadiensis HD146
B. thuringiensis var. toumanoffi HD201
B. thuringiensis var. kyushuensis HD541
B. thuringiensis var. thompsoni HD542
B. thuringiensis var. pakistani HD395
B. thuringiensis var. israelensis HD567
B. thuringiensis var. indiana HD521
B. thuringiensis var. dakota
B. thuringiensis var. tohokuensis HD866
B. thuringiensis var. kumanotoensis HD867
B. thuringiensis var. tochigiensis HD868
B. thuringiensis var. colmeri HD847
B. thuringiensis var. wuhanensis HD525
Bacillus cereus—ATCC 21281
Bacillus moritai—ATCC 21282
Bacillus popilliae—ATCC 14706
Bacillus lentimorbus—ATCC 14707
Bacillus sphaericus—ATCC 33203
Beauveria bassiana—ATCC 9835
Metarrhizium anisopliae—ATCC 24398
Metarrhizium flavoviride—ATCC 32969
Streptomyces avermitilus—ATCC 31267

The method of treating the organism can fulfill a number of functions. First, it may enhance structural integrity. Second, it may provide for enhanced proteolytic stability of the toxin, by modifying the toxin so as to reduce its susceptibility to proteolytic degradation and/or by reducing the proteolytic activity of proteases naturally present in the cell. The cells are preferably modified at an intact stage and when there has been a substantial build-up of the toxin protein. These modifications can be achieved in a variety of ways, such as by using chemical reagents having a broad spectrum of chemical reactivity. The intact cells can be combined with a liquid reagent medium containing the chemical reagents, with or without agitation at temperatures in the range of about $-10°$ to $60°$ C. The reaction time may be determined empirically and will vary widely with the reagents and reaction conditions. Cell concentrations will vary from about $10E^2$ to $10E^{10}$ per ml.

Of particular interest as chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W.H. Freeman and Company, 1967); or a combination of physical (heat) and chemical agents that prolong the activity of the toxin produced in the cell when the cell is applied to the environment of the target pest(s).

For halogenation with iodine, temperatures will generally range from about $0°$ to $50°$ C., but the reaction can be conveniently carried out at room temperature. Conveniently, the iodination may be performed using triiodide or iodine at 0.5 to 5% in an acidic aqueous medium, particularly an aqueous carboxylic acid solution that may vary from about 0.5–5 M. Conveniently, acetic acid may be used, although other carboxylic acids, generally of from about 1 to 4 carbon atoms, may also be employed. The time for the reaction will generally range from less than a minute to about 24 hrs, usually from about 1 to 6 hrs. Any residual iodine may be removed by reaction with a reducing agent, such as dithionite, sodium thiosulfate, or other reducing agent compatible with ultimate usage in the field. In addition, the modified cells may be subjected to further treatment, such as washing to remove all of the reaction medium, isolation in dry form, and formulation with typical stickers, spreaders, and adjuvants generally utilized in agricultural applications, as is well known to those skilled in the art.

Of particular interest are reagents capable of cross-linking the cell wall. A number of reagents are known in the art for this purpose. The treatment should result in enhanced stability of the pesticide. That is, there should be enhanced persistence or residual activity of the pesticide under field conditions. Thus, under conditions where the pesticidal activity of untreated cells diminishes, the activity of treated cells remains for periods of from 1 to 3 times longer.

The cells can be formulated for use in the environment in a variety of ways. They can be employed as wettable powders, granules, or dusts, by mixing with various inert materials, such as inorganic minerals (phyllosilicates, carbonates, sulfates, or phosphates) or botanical materials (powdered corncobs, rice hulls, or walnut shells). The formulations can include spreader/sticker adjuvants, stabilizing agents, other pesticidal additives, or surfactants. Liquid formulations can be aqueous-based or non-aqueous and employed as foams, gels, suspensions, emulsifiable concentrates, and the like. The ingredients can include rheological agents, surfactants, emulsifiers, dispersants, polymers, and the like.

The pesticidal concentration will vary depending upon the nature of the particular formulation, e.g., whether it is a concentrate or to be used undiluted. The pesticide will generally be present at a concentration of at least about 1% by weight, but can be up to 100% by weight. The dry formulations will have from about 1 to 95% by weight of the pesticide, while the liquid formulations will generally be from about 1 to 60% by weight of the solids in the liquid phase. The formulations will generally have from about 1E2 to 1E8 cells/mg.

The formulations can be applied to the environment of the pest(s), e.g., plants, soil or water, by spraying, dusting, sprinkling or the like. These formulations can be administered at about 2 oz (liquid or dry) to 2 or more pounds per hectare, as required.

The following examples are offered by way of illustration and not by way of limitation.

EXAMPLE 1

After treatment of intact spore-containing cells (prior to autolysis) of *B. thuringiensis* with lugol's iodine, the cells are killed; however, they retain toxicity to *Trichoplusia ni* larvae.

The intact cells of Bacillus thuringiensis (HD-1) were harvested just prior to autolysis of the sporulating cells by centrifugation and the cell pellet suspended in deionized water to give a concentration of $6.0 \times 10E9$ cells/ml. An aliquot of the cell suspension was diluted to $1.5 \times 10E8$ cells/ml and exposed to 1% lugol's iodine for 4 hr at room temperature (a 1% lugol's solution contains 1.0 g potassium iodide, 0.5 g iodine and 1.0 ml glacial acetic acid per liter.) The treated cells were washed and resuspended in sterile deionized water to give a cell concentration of $6.0 \times 10E9$. No viable cells were detected by plate counts on nutrient agar after the 4 hr iodine treatment. Lugol's treated and untreated control cells were then bioassayed for toxicity to *T. ni* larvae.

Since the cells of the subject invention are naturally-occurring cells, it would not be necessary to treat them under killing conditions in order to realize the benefits of the subject invention. Thus, treatment of the cells, as described herein, can be optimized by a person skilled in the art to achieve the highest level of prolongation of toxin (pesticidal) activity in the environment of the target pest(s).

Bioassay procedure

Dilutions of lugol's killed cells or untreated live HD-1 cells were mixed with a constant volume of larval diet cup. A single 5 day old *T. ni* larva was then added to each cup. Eighteen larvae were tested per dilution. The larvae were examined after six days and the total number of larvae killed was recorded. The results are shown in Table 1. They are given in percent larvae killed.

TABLE 1

| Bioassay of Lugol's-Treated Intact Spore-Containing *Bacillus thuringiensis* (HD-1) Cells | | | | | |
|---|---|---|---|---|---|
| Cell Dilution | 10E9 | 10E8 | 10E7 | 10E6 | 10E5 |
| HD-1 Untreated | 100 | 100 | 68.8 | 0 | 0 |
| Lugol's Treated | 94.4 | 61.0 | 0 | 0 | 0 |

EXAMPLE 2

Stability Testing

Intact, spore-containing cells of *B.t.* HD-1 were treated with 1% lugol's solution for 4 hr at room temperature, washed in deionized water, and stored in the refrigerator for 52 days. After this period the cells remained whole, and there was no evidence of lysis (release of spores and crystal).

Intact, spore-containing cells of *B.t.* HD-1 were harvested by centrifigation and the resulting pellet suspended in sterile deionized water (10E10 cells/ml), heated to 70° C. for 30 min, and stored in the refrigerator for 9 days. After this period, virtually all of the cells have lysed, releasing spores and crystals.

EXAMPLE 3

Soil Experiment Procedure

*B.t.* HD-1 preparation

An intact spore-containing culture of *B.t.* HD-1 was harvested by centrifugation and the cell pellet resuspended in 400 ml of 1% lugol's iodine (4×10E8 cells/ml). The iodine-cell suspension was stirred for 3 hr at room temperature, washed 3 times and resuspended in 400 ml sterile 0.1 M sodium phosphate buffer, pH 6.9. No viable *B.t.* HD-1 cells were detected on nutrient agar (10E-1) after treatment with iodine, and microscopic examination revealed that all cells were intact (unlysed).

Dipel preparation

Dipel (0.1 g, Abbott Laboratories, 16,000 International Units of Potency/mg. List #5188) was measured into 400 ml of sterile 0.1 M sodium phosphate buffer.

Experimental Design (1) Non-sterile soil preparation: 40 g of soil was placed in a sterile 500 ml flask and 200 ml of experimental solution added.

(2) Sterile soil preparation: 40 g of soil was placed in a sterile 500 ml flask and autoclaved for 1 hr prior to adding 200 ml of experimental solution. Flasks containing soil suspensions were incubated on a gyratory shaker (200 RPM) at room temperature. Samples (30–40 ml) of each soil suspension were filtered through 4x cheesecloth and sprayed onto the leaves of lettuce plants for subsequent measurement of toxicity against larvae of *T. ni.*

Measurement of *B.t.* Toxin by Feeding Inhibition

Leaves of Romaine lettuce seedlings are sprayed with freshly prepared standard concentrations of Dipel (1x 0.19 g/100 ml, 1/10x, 1/20x, and 1/100x), and experimental solutions 24 hr before use.

Leaves treated with standards or experimental solutions are removed from the plant, weighed individually, and placed in individual petri dishes. Ten starving, 7 day old *T. ni* larvae are applied to each leaf and allowed to feed on the leaf for approximately 24 hrs at 25° C. At the end of the feeding period the leaves are re-weighed and the average weight loss determined for each treatment.

Under the conditions described above, leaf weight loss is a log linear function of toxin concentration over concentrations of toxin equivalent to 0.19 mg/ml–0.019 mg/ml Dipel (16,000 international units of potency per mg). Thus, the freshly prepared Dipel concentrations sprayed onto lettuce plants and run with each assay serve as standards by which the concentration of *B.t.* HD-1 toxin on leaves sprayed with experimental solutions can be equated. The data in Table 2 show the percentage of the original toxicity (day 1) remaining at various times after incubation.

TABLE 2

Persistence of Toxicity in Soil
% of Original Toxicity Remaining

| Days After Start of Soil Incubation | Dipel (Spore Crystal Preparation) | | Pre-Lysed Lugol's Iodine Treated B.t. HD-1 (Whole Cell Preparation) | |
|---|---|---|---|---|
| | Sterile | Nonsterile | Sterile | Nonsterile |
| 1 | 100 | 100 | 100 | 100 |
| 5 | 81 | 0.5 | 133 | 100 |
| 8 | 74 | 5.3 | 80 | 76 |
| 15 | — | — | 87 | 117 |

Inactivation of the protein-crystal of *B.t.* HD-1 in soil has been shown to be due to the activity of soil microorganisms. (West, 1984). The results of Table II demonstrate that when Dipel and a lugol's iodine treated pre-lysed *B.t.* HD-1 preparation were incubated under similar conditions, the toxicity of the Dipel (spore-crystal) preparation degenerated rapidly, while the toxicity of the lugol's iodine treated cells remained essentially unchanged.

It is evident from the above results that chemical treatment of whole microbial cells can be performed in such a way as to retain polypeptide toxin activity, while rendering the cell stable to storage conditions. This provides increased residual activity of toxin activity under field conditions.

Although the foregoing invention has been described in some detail by way of illustration and example for purposes of clarity of understanding, it will be obvious that certain changes and modifications may be practiced within the scope of the appended claims.

We claim:

1. An improved pesticidal composition comprising a substantially intact microorganism naturally producing a pesticide, said microorganism stabilized to have prolonged pesticidal activity when applied to the environment of a target pest; and an inert carrier.

2. A pesticidal composition, according to claim 1, wherein said substantially intact microorganism is stabilized with a halogenating agent.

3. A pesicidal composition, according to claim 2, wherein said halogenating agent is lugol's iodine.

4. A pesticidal composition, according to claim 1, wherein said microorganism is a Bacillus.

5. A pesticidal composition, according to claim 4, wherein said Bacillus is a pesticide-producing species of *Bacillus thuringiensis.*

6. A pesticidal composition, according to claim 5, wherein said pesticide-producing species of *Bacillus thuringiensis* is selected from the group consisting of *B. thuringiensis* M-7, *B. thuringiensis* var. *kurstaki* HD1, *B. thuringiensis* HD2, *B. thuringiensis* var. *finitimus* HD3, *B. thuringiensis* var. *alesti* HD4, *B. thuringiensis* var. *kurstaki* HD73, *B. thuringiensis* var. *sotto* HD770, *B. thuringiensis* var. *dendrolimus* HD7, *B. thuringielsis* var. *kenyae* HD5, *B. thuringiensis* var. *galleriae* HD29, *B. thuringiensis* var. *canadensis* HD224, *B. thuringiensis* var. *entomocidus* HD9, *B. thuringiensis* var. *subtoxicus* HD109, *B. thuringiensis* var. *aizawai* HD11, *B. thuringiensis* var. *morrisoni* HD12, *B. thuringiensis* var. *ostriniae* HD501, *B. thuringiensis* var. *tolworthi* HD537, *B. thuringiensis* var. *darmstadiensis* HD146, *B. thuringiensis* var. *toumanoffi* HD201, *B. thuringiensis* var. *kyushuensis* HD541, *B. thuringiensis* var. *thompsoni* HD542, *B. thu-*

*ringiensis* var. *pakistani* HD395, *B. thuringiensis* var. *israelensis* HD567, *B. thuringiensis* var. *indiana* HD521, *B. thuringiensis* var. *dakota, B. thuringiensis* var. *tohokuensis* HD866, *B. thuringiensis* var. *kumanotoensis* HD867, *B. thuringiensis* var. *tochigiensis* HD868, *B. thuringiensis* var. *colmeri* HD847, and *B. thuringiensis* var. *wuhanensis* HD525.

7. A pesticidal composition, according to claim 4, wherein said Bacillus is selected from the group consisting of *B. cereus, B. moritai, B. popilliae, B. lentimorbus, and B. sphaericus.*

8. A pesticidal composition, according to claim 1, wherein said microorganism is an entomopathogenic fungus.

9. A pesticidal composition, according to claim 8, wherein said entomopathogenic fungus is *Beauveria bassiana* or Metarrhizium spp.

10. A pesticidal compositon, according to claim 1, wherein said microorganism is a Streptomyces.

11. A pesticidal composition, according to claim 10, wherein said Streptomyces is *Streptomyces avermitilus.*

12. A pesticidal composition, according to claim 1, wherein said pesticide is a polypeptide.

13. A method for protecting a host susceptible to an invertebrate pest which comprises inhibiting said pest by use of a pesticidal composition, said pesticidal composition comprising a naturally-occurring pesticide-producing substantially intact microorganism wherein said microorganism is stabilized while intact to prolong the pesticidal activity when said pesticide-producing microorganism is applied to the environment of said target pest.

14. A method, according to claim 13, wherein said substantially intact microorganism is stabilized with a halogenating reagent.

15. A method, according to claim 14, wherein said halogenating reagent is lugol's iodine.

16. A method, according to claim 13, wherein said microorganism is a Bacillus.

17. A method, according to claim 16, wherein said Bacillus is a pesticide-producing specie of *Bacillus thuringiensis.*

18. A method, according to claim 17, wherein said pesticide-producing specie of *Bacillus thuringiensis* is selected from the group consisting of *B. thuringiensis* M-7, *B. thuringiensis* var. *kurstaki* HD1, *B. thuringiensis* HD2, *B. thuringiensis* var. *finitimus* HD3, *B. thuringiensis* var. *alesti* HD4, *B. thuringiensis* var. *kurstaki* HD73, *B. thuringiensis* var. *sotto* HD770, *B. thuringiensis* var. *dendrolimus* HD7, *B. thuringiensis* var. *kenyae* HD5, *B. thuringiensis* var. *galleriae* HD29, *B. thuringiensis* var. *canadensis* HD224, *B. thuringiensis* var. *entomocidus* HD9, *B. thuringiensis* var. *subtoxicus* HD109, *B. thuringiensis* var. *aizawai* HD11, *B. thuringiensis* var. *morrisoni* HD12, *B. thuringiensis* var. *ostriniae* HD501, *B. thuringiensis tolworthi* HD537, *B. thuringiensis* var. *darmstadiensis* HD146, *B. thuringiensis* var. *toumanoffi* HD201, *B. thuringiensis* var. *kyushuensis* HD541, *B. thuringiensis* var. *thompsoni* HD542, *B. thuringiensis* var. *pakistani* HD395, *B. thuringiensis* var. *israelensis* HD567, *B. thuringiensis* var. *indiana* HD521, *B. thuringiensis* var. *dakota, B. thuringiensis* var. *tohokuensis* HD866, *B. thuringiensis* var. *kumanotoensis* HD867, *B. thuringiensis* var. *tochigiensis* HD868, *B. thuringiensis* var. *colmeri* HD847, and *B. thuringiensis* var. *wuhanensis* HD525.

19. A method, according to claim 16, wherein said Bacillus is selected from the group consisting of *B. cereus, B. moritai, B. popolliae, B. lentimorbus,* and *B. sphaericus.*

20. A method, according to claim 13, wherein said pesticide is a polypeptide produced by a naturally-occurring microorganism.

* * * * *